United States Patent [19]

Conard et al.

[11] Patent Number: 4,936,449

[45] Date of Patent: Jun. 26, 1990

[54] DISPOSABLE SHARPS RETAINING AND DISPOSAL DEVICE

[76] Inventors: Douglas S. Conard; Barbara B. Conard, both of 8698 Lafayette Rd., Indianapolis, Ind. 46278; Victor A. DeRose, 7600 Sargent Rd., Indianapolis, Ind. 46256

[21] Appl. No.: 268,373

[22] Filed: Nov. 7, 1988

[51] Int. Cl.$^5$ .............................. A61L 2/16; B65F 1/00
[52] U.S. Cl. .................................... 206/366; 206/382; 211/60.1; 220/1 T
[58] Field of Search ............... 206/366, 365, 380, 364, 206/363, 367, 382, 383; 211/60.1, 86; 604/110, 199; 220/1 T

[56] References Cited

U.S. PATENT DOCUMENTS

| 537,683 | 4/1895 | Hare | 220/315 |
|---|---|---|---|
| 978,251 | 12/1910 | Whitney | 220/315 |
| 2,313,905 | 3/1943 | Wallin | 211/60.1 |
| 2,493,086 | 2/1949 | Reifsnyder | 220/306 |
| 2,568,405 | 9/1951 | O'Malley | 211/60.1 |
| 2,591,349 | 4/1952 | Coebel | 211/60.1 |
| 2,903,129 | 9/1959 | Anderson, III | 206/363 |
| 3,876,067 | 4/1975 | Schwarz | 206/366 |
| 4,008,802 | 2/1977 | Freitag | 206/382 |
| 4,106,621 | 8/1978 | Sorenson | 206/365 |
| 4,151,913 | 5/1979 | Freitag | 206/382 |
| 4,375,849 | 3/1983 | Hanifi . | |
| 4,380,292 | 4/1983 | Cramer | 206/63.5 |
| 4,454,944 | 6/1984 | Shillington et al. | 206/380 |
| 4,488,643 | 12/1984 | Pepper | 206/366 |
| 4,520,926 | 6/1985 | Nelson | 206/366 |
| 4,637,513 | 1/1987 | Eldrige, Jr. | 206/380 |
| 4,802,579 | 2/1989 | Hall et al. | 206/366 |
| 4,804,090 | 2/1989 | Schuh et al. | 206/366 |
| 4,807,344 | 2/1989 | Kelson et al. | 206/366 |
| 4,836,373 | 6/1989 | Goldman | 206/366 |
| 4,844,249 | 7/1989 | Coulombe | 206/365 |

FOREIGN PATENT DOCUMENTS

| 0018120 | 10/1916 | Fed. Rep. of Germany | 206/363 |
|---|---|---|---|
| 2227428 | 4/1980 | Fed. Rep. of Germany | 206/366 |

Primary Examiner—Paul T. Sewell
Assistant Examiner—Jacob K. Ackun, Jr.
Attorney, Agent, or Firm—Barnes & Thornburg

[57] ABSTRACT

A block of, for example, styrofoam for penetration by, and for frictionally holding, disposable hypodermic needles, scalpels and other sharps, is held in a container including a bottom and a sidewall. Pawl-shaped projections are provided adjacent the upper lip of the sidewall. A lid includes complementary pawl-shaped projections adjacent its lower lip for engagement with respective projections on a contaminant neutralizing substance such as BETADINE, or another layer of, for example, wadding, located above or below the styrofoam can be saturated with the contaminant neutralizing substance.

7 Claims, 3 Drawing Sheets

DISPOSABLE SHARPS RETAINING AND DISPOSAL DEVICE

This invention relates to systems for the disposal of contaminated disposable sharp medical instruments, generally referred to in the medical field, and referred to hereinafter, as sharps. Sharps is a term that encompasses, for example, disposable hypodermic syringes with affixed needles, disposable scalpels, trocars, angiocatheter kits and other sharp objects used to penetrate the body for medical, dental or veterinary treatment purposes. Herein these fields are referred to collectively as the medical field.

Prior art in the field of disposal systems for sharps includes systems of the type described in U.S. Pat. No. 4,375,849. Such systems seek to provide rugged containers into which used, contaminated disposable sharps can be deposited for disposal. Major concerns are to provide such disposal systems which reduce to the extent reasonably obtainable the likelihood that the contaminated sharps will subsequently accidentally puncture someone and that contaminants will escape from the disposal container. Reducing this likelihood reduces the likelihood that these contaminants will infect medical service providers and others. Reducing this likelihood thus is a significant contribution since these contaminants can include, for example, human immunodeficiency virus (AIDS) and type B (serum) hepatitis virus.

A significant problem with prior art of the type exemplified by U.S. Pat. No. 4,375,849 is that, as the containers of these systems fill up with sharps, the sharp portions of these, such as needles and blades, can become accessible through the openings through which contaminated sharps are deposited into them. This can result in accidental sticks with these contaminated sharps and resulting infection. There are occasional reports of the tragic results of such accidental sticks.

In addition, filling up of these containers makes contaminated sharps accessible through the container lids. It is an unfortunate fact that there are those who will remove these contaminated sharps from these disposal containers and either reuse them themselves or provide them to others, and so pass along whatever diseases contaminate them.

Some prior art systems include needle-breaking devices. However, such devices are regarded as unsatisfactory because they frequently simply create another contaminated sharp, the broken needle. In addition, such systems frequently generate contaminant aerosols containing whatever the needles have in them in the process of breaking needles.

The prior art also includes systems of the type illustrated in FIG. 1. That system is provided with a container 1 including a bottom 2 and a hinged lid 3. A snap closure 4 permits the bottom 2 and lid 3 to be retained in closed orientation. A magnetic liner 5 lines bottom 2 to retain contaminated ferromagnetic sharps 6 on the liner 5. Some of sharps 6 may not be ferromagnetic, and thus may not be retained securely on liner 5. Strips 7 of, for example, polystyrene foam are attached, for example by a suitable adhesive, to the inside 8 of lid 3 to insure that sharps 6 disposed of on liner 5 are held in place when lid 3 is closed and do not shift around inside the closed container 1. Such shifting can expose medical service personnel carrying container 1 to sticks from sharps 6 which shift around inside container 1 and inadvertently project out of container 1 between bottom 2 and lid 3. In addition, there is the possibility that, if container 1 is left lying around with contaminated sharps in it, it can be opened and the contaminated sharps removed. The size of container 1 is such that disposable sharps frequently have to be disassembled to fit into it, such as by removing needles from hypodermic syringes, removing blades from disposable scalpels, and so on. This additional handling of the contaminated sharps, of course, increases the likelihood of an accidental stick.

It is an object of the invention to overcome, to the extent possible, some of the weaknesses of the prior art sharps disposal systems. In its broadest aspect, the invention comprises a block of material for penetration by, and for frictionally holding, contaminated sharps for disposal, thereby reducing the likelihood of subsequent accidental punctures to medical service providers and the like.

Illustratively according to an embodiment of the invention, the block comprises a bottom surface and means for adhesively mounting the block to a supporting surface, the adhesive mounting means provided on the bottom surface.

According to an illustrative embodiment, the block includes a flexible strap extending from the block and means on the block for engagement by the strap. Placement of the block on a supporting surface followed by placement of the strap around the supporting surface and engagement of the means on the block by the strap attaches the block to the supporting surface.

According to other embodiments of the invention, the apparatus further comprises a container for housing the block and for reducing the likelihood of subsequent accidental puncture to medical service providers or the like by the sharps or escape of contaminants such as contaminated sharps or body fluids, the container having a bottom and a sidewall extending from the bottom.

According to some embodiments, the apparatus further comprises means for adhesively mounting the container or block to a supporting surface, the adhesive mounting means being provided on the outside of the bottom or side of the container.

Additionally according to some embodiments, the adhesive mounting means comprises a piece of double-sided adhesive, one side of which adhesively engages the bottom or side of the container or block and the other side of which is covered by a peel-off protective strip.

According to certain embodiments of the invention, the apparatus further comprises a lid for the container. The container includes first engagement means and the lid includes second engagement means for engaging the first engagement means to reduce the likelihood of disengagement of the lid from the container once the two are engaged. This reduces the likelihood of removal of contaminated sharps therefrom and also reduces the likelihood of accidental puncture to medical service providers or the like or escape of contaminants from the container with the lid engaged thereon.

Illustratively, according to certain embodiments of the invention, the lid comprises a top and a sidewall extending from the top, the container sidewall comprising the first engagement means and the lid sidewall comprising the second engagement means, the container sidewall and lid sidewall tightly engaging each other when the lid is in place on the container to reduce the likelihood of removal of contaminated sharps therefrom and to reduce the likelihood of accidental puncture to medical service providers or the like or escape of contaminants from the container with the lid engaged thereon.

According to some embodiments of the invention, the container sidewall has a first depth and the lid sidewall has a second depth greater than the first depth.

According to an illustrative embodiment, the container further comprises a flexible strap extending from the sidewall and means on the sidewall for engagement by the strap. Placement of the container on a supporting surface followed by placement of the strap around the supporting surface and engagement of the means on the sidewall by the strap attaches the container to the supporting surface.

According to several embodiments of the invention, the apparatus further comprises a contaminant-neutralizing substance for impregnating the block to reduce further both the likelihood of injury from contaminated sharps which have previously been brought into contact with the contaminant-neutralizing substance and the likelihood of escape of contaminants from the block.

According to some embodiments, the apparatus further comprises a second impregnable material located in the container and a contaminant-neutralizing substance for impregnating the second material to reduce further both the likelihood of injury from contaminated sharps which have previously been brought into contact with the contaminant-neutralizing substance and the likelihood of escape of contaminants from the container.

According to some embodiments, the block forms a first layer in the container, the second material forms a second layer, and the second layer is positioned in the container between the first layer and the bottom. According to other embodiments, the first layer is positioned in the container between the second layer and the bottom.

The invention may best be understood by referring to the following detailed descriptions of illustrative embodiments and the accompanying drawings which illustrate these various embodiments. In the drawings:

FIG. 2 illustrates in perspective a simple embodiment of the invention resting on an armboard of a bed, table, attachment to an intravenous tripod stand, gurney, or the like;

Figure 1:
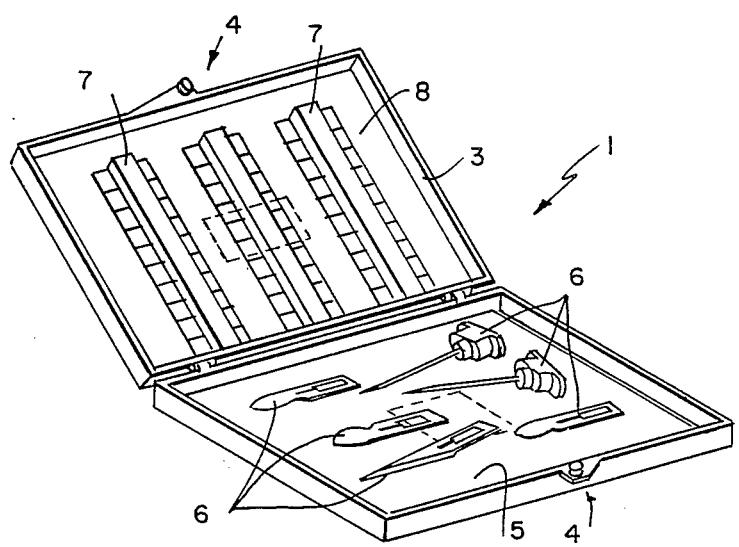
FIG. 1 illustrates a perspective view of a prior art sharps disposal container in open orientation.
Figure 2:
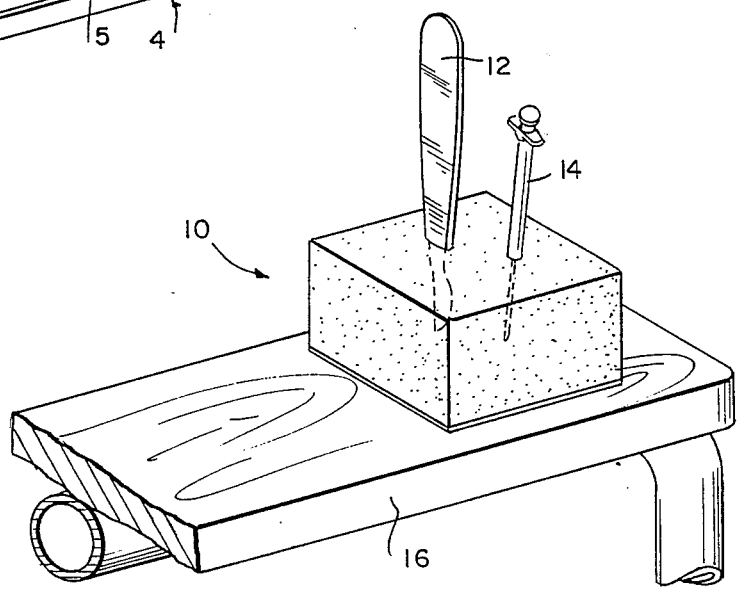

Referring now particularly to FIG. 2, the invention in its simplest form comprises a block 10 of a material such as polystyrene foam which is penetrable by, and capable of frictionally holding, contaminated disposable sharps such as a disposable scalpel 12 and a disposable hypodermic syringe and needle 14. Block 10 is of sufficient size and mass that it can rest as illustrated at 16 at the bedside or on an armboard of a hospital bed, operating table, attachment to an intravenous tripod stand, gurney, or the like. The material from which block 10 is formed is somewhat absorbent so that liquid contaminants, such as blood and other body fluids with which sharps 12, 14 are contaminated, are less likely to leak from block 10. To increase the mass of block 10, it can be weighted by, for example, a slug or plate of a heavy metal or the like inserted, cast, or adhesively bonded into or onto block 10.

Figure 3:
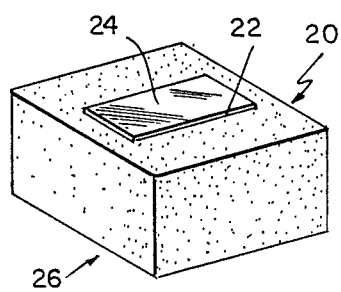
FIG. 3 illustrates a perspective view of an embodiment of the invention turned upside down.

In the embodiment of FIG. 3, a block 20 of such material is provided with a strip 22 of a double-sided adhesive tape. A paper strip 24 protects one adhesive surface of strip 22. The other adhesive surface of strip 22 is secured to the flat bottom 26 of block 20. When the block 20 is to be used, the medical service provider simply removes strip 24, activating the adhesive on the bottom side of strip 22, turns block 20 to a suitable orientation, and sticks block 20 to the appropriate surface of an armboard or the like.

Figure 4:
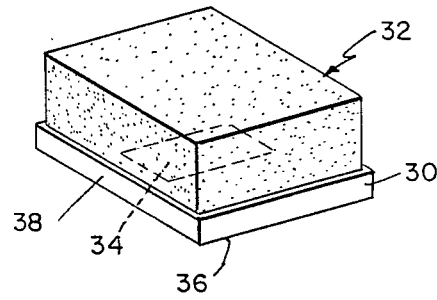
FIG. 4 illustrates a perspective view of another embodiment of the invention.

In the embodiment of the invention illustrated in FIG. 4, a shallow container 30 encloses the bottom portion of the block 32 of absorbent and frictional holding material. The double-sided adhesive strip 34 in this embodiment is mounted on the outside surface (that is, the side facing away from block 32) of the bottom 36 of container 30. Container 30 also includes a shallow sidewall 38 extending upwardly generally perpendicularly from the perimeter of bottom 36. Container 30 reduces the likelihood that sharps will accidentally protrude from the bottom portion of block 32 or that contaminants will leak from block 32, since the container 30 also forms a sort of basin for the bottom portion of block 32.

Figure 5:
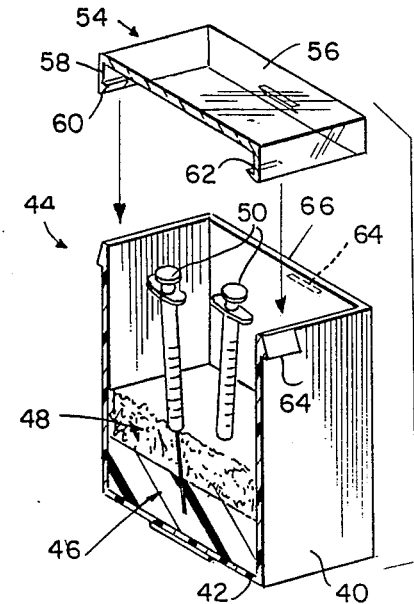
FIG. 5 illustrates a vertically sectioned and exploded perspective view of another embodiment of the invention.

In the embodiment illustrated in FIG. 5, a deeper sidewall 40 extends upward from the bottom 42 of the container 44. The layer 46 of frictional material, again such as polystyrene foam, is interposed between the bottom 42 and a second layer 48 of absorbent wadding such as cotton or other cellulosic wadding. Layer 48 is impregnated or saturated with an antimicrobial, antiviral material which neutralizes the contaminants with which used disposable sharps 50 are contaminated. Such a material might be, for example, hydrogen peroxide, glutaraldehyde, chlorine bleach, an iodinated disinfectant, or one of the commercially available proprietary disinfectants such as BETADINE disinfectant. As the sharps 50 are inserted through the layer 48 into the layer 46, an amount of the neutralizing agent contacts the surfaces of the sharps and the contaminants with which these surfaces are contaminated. Additionally, if the layer 48 is saturated, some of the neutralizing agent may migrate into layer 46 causing portions of the contaminated sharps 50 to be exposed for extended periods of time to neutralizing agent in layer 46 as well.

Container 44 is provided with a lid 54 having a top 56 and a generally perpendicularly downwardly extending sidewall 58. The lower lip 60 of sidewall 58 is provided with a pawl-shaped cross section portion 62 which engages pawl-shaped cross section portions 64 provided at the upper extent 66 of sidewall 40. Container 44 and lid 54 illustratively are molded from highly resilient high impact resins so that they can be snapped together to capture contaminated sharps 50 to reduce the likelihood of removal of the contaminated sharps 50 as well as reducing the likelihood of leakage of contaminants from container 44.

Figure 6:
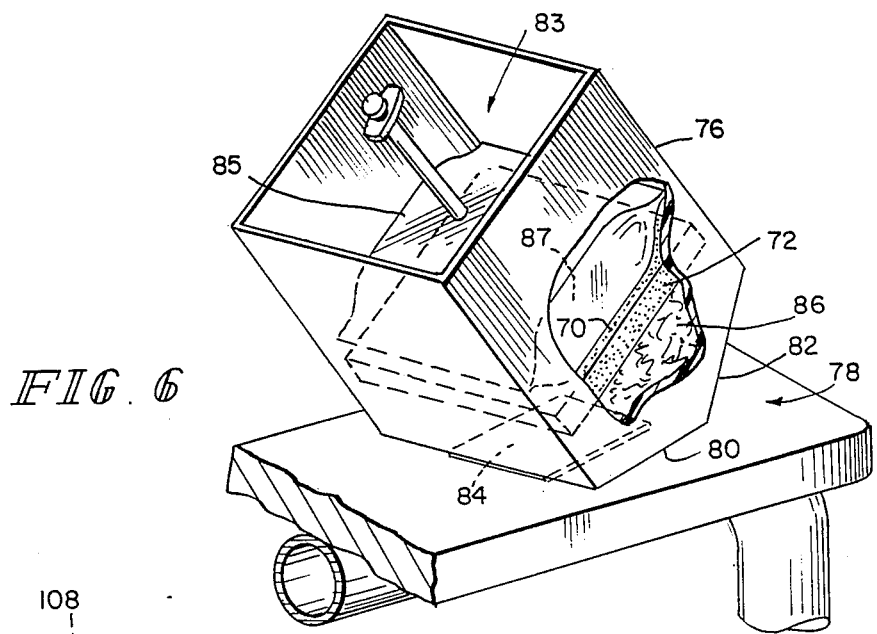
FIG. 6 illustrates a perspective view, partly broken away, of another embodiment of the invention mounted on an armboard of a table.

In all of the embodiments illustrated thus far, the blocks of material for holding the sharps and the containers for these have been illustrated as generally right rectangular prisms. It will be appreciated that other shapes can be employed and that certain benefits are available with other shapes under certain circumstances. For example, the treating medical service provider may find it convenient under certain circumstances to have the surface 70 (FIG. 6) of a block 72 of sharps-holding material at an angle to horizontal. That might be the case, for example, where the medical task to be performed calls for the essentially continuous attention of the medical service provider who thus cannot look up from the task but very briefly. In the embodiment illustrated in FIG. 6, the container 76 has a somewhat V-shaped bottom 78 formed by intersecting bottom walls 80, 82. Wall 80 is provided with a strip 84 of double-sided adhesive to attach container 76 to an armboard or the like. In this embodiment, a layer 86 of absorbent wadding is interposed between the bottom 78 of container 76 and block 72.

Wadding 86 need not be saturated with contaminant-neutralizing material In this embodiment, a separate packet 83 having a sharps-penetrable envelope 85, for example of plastic or metal film or foil, contains a separate wadding 87 which is impregnated with a contaminant-neutralizing agent. At the beginning of a medical procedure, the packet 83 is simply placed into container 76 on top of surface 70.

Figure 7:
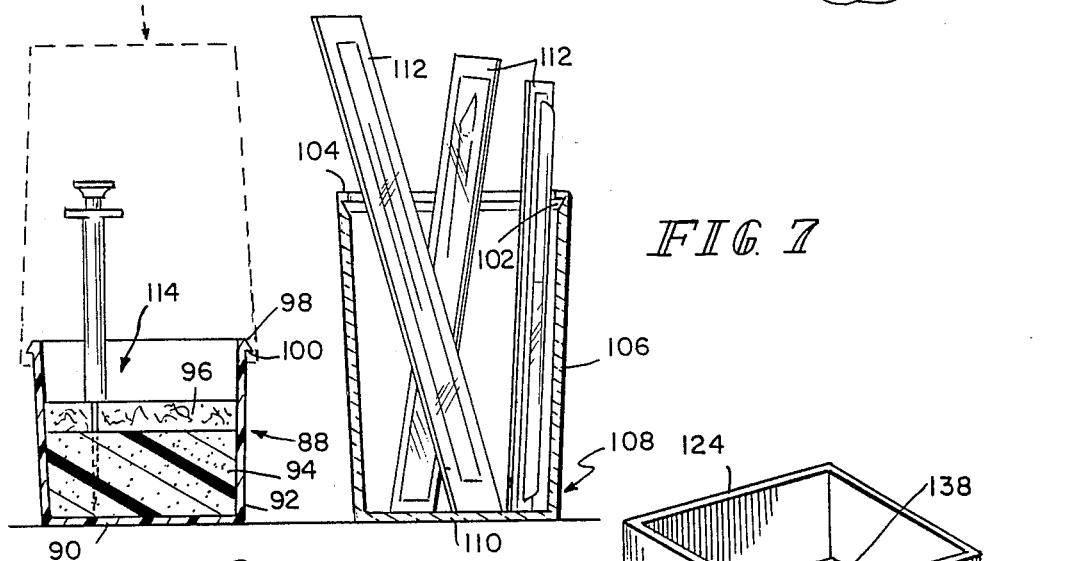
FIG. 7 illustrates a vertically sectioned side elevational view of another embodiment of the invention.

Referring now to FIG. 7, a container 88 having a bottom 90 and sidewall 92 is illustrated. Container 88 houses a layer 94 of frictional sharps holding material and a layer 96 of material saturated with an antimicrobial contaminant-neutralizing agent. In this embodiment, layer 94 is interposed between the bottom 90 and layer 96. The upper lip 98 of sidewall 92 is provided with outwardly extending pawl-shaped cross-section portions 100 for engaging pawl-shaped cross-section grooves 102 provided inside the lower lip 104 of the sidewall 106 of a lid 108. Lid 108 includes a top 110 from the perimeter of which sidewall 106 extends. Lid 108 is illustrated inverted in FIG. 7, illustrating that the lid 108 can be used to carry and hold various medical equipment and kits 112, such as disposable scalpels, hypodermic syringes and needles, I.V. kits and so on, to the site of the medical procedure, with the equipment being used at the site and disposed of in the container 88. Then the lid 108 which has thus been emptied can be turned upright and snapped onto the container 88 to close it and reduce the likelihood that sharps 114 which have been contaminated during the medical procedure will be removed from container 88 or leak contaminants when the container 88 is disposed of. To promote the utility of this embodiment for the effective disposal of such sharps as hypodermic syringes, disposable scalpels and the like having long handles or non-sharps portions, the sidewall 106 of lid 108 is substantially deeper than the sidewall 92 of container 88.

Figures 8, 9:
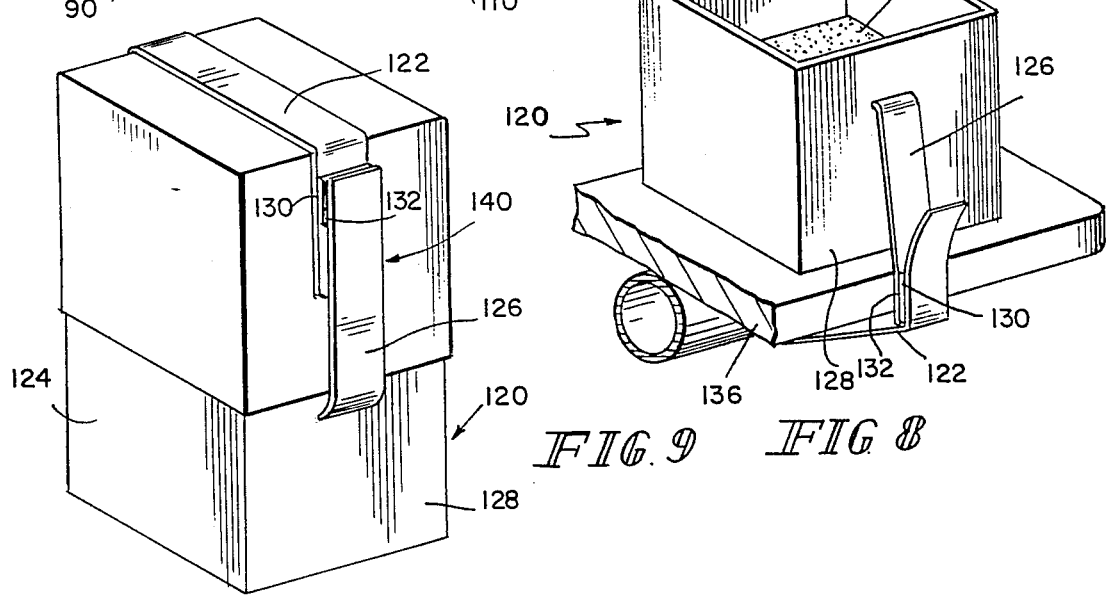
FIG. 8 illustrates in perspective a portion of another embodiment of the invention mounted on an armboard of a table.
FIG. 9 illustrates an assembled perspective view of the embodiment illustrated in FIG. 8.

In the embodiment of FIGS. 8-9, the container 120 is provided with a flexible strap 122 on sidewall surface 124 and a flexible strap 126 on sidewall surface 128. Straps 122, 126 illustratively can be formed from some tough, flexible resinous material and can be attached to surfaces 124, 128 by suitable adhesives. Alternatively, if container 120 is formed from a tough, high-impact but flexible resinous material, it may be advantageous to form straps 122, 126 from the same material in the same operation, such as molding, during which container 120 is formed. The straps 122, 126 are provided with means, such as VELCRO-type synthetic hook and eyelet material strips 130, 132, for fastening them together. In FIG. 8, straps 122, 126 are fastened together around an armboard 136, securing the container 120 to the armboard for the convenience of the medical service provider in inserting contaminated sharps into and/or through the layer 138. In FIG. 9, straps 122, 126 are fastened together around a lid 140 with which container 120 is provided to reduce the likelihood of contaminated sharps or contaminants being removed or spilling or leaking. As with the embodiments discussed previously, lid 140 is a tight friction fit on container 120. The material from which the container is formed can be opaque, translucent or transparent as dictated by the application. If the container is generally transparent, it is easier to inventory the contents of the container. The container can be provided with a peel-off seal during manufacture to prevent evaporation of volatile contaminant-neutralizing agents.

Figure 10:
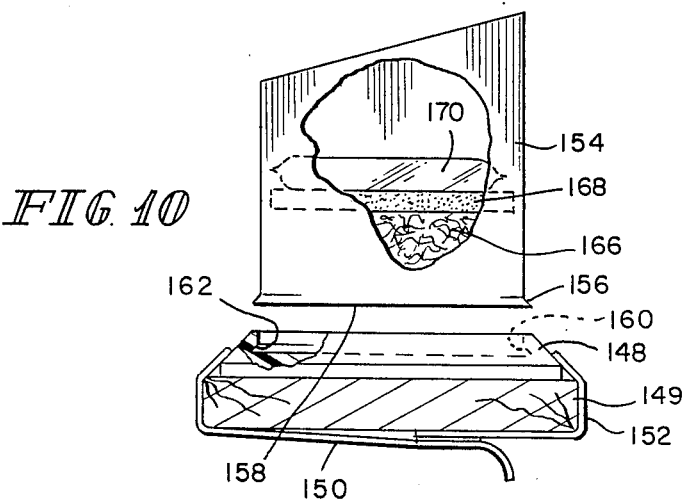
FIG. 10 illustrates a partly sectional, partly broken away side elevational view of another embodiment of the invention.

In the embodiment illustrated in FIG. 10, a container base 148 is secured to an armboard 149 by straps 150, 152. The ends of straps 150, 152 remote from base 148 may be provided with VELCRO-type strips to attach them together. The container 154 in this embodiment is provided with an outwardly projecting flange 156 around its bottom 158. Flange 156 is designed to engage a groove 160 around a central opening 162 in base 148. Container 154 is constructed from a resiliently deformable plastic material so that flange 156 snaps into and out of engagement in groove 160. Container 154 houses a bottom layer 166 of cellulosic wadding, a middle layer 168 of frictional material such as polystyrene foam, and, on top, a packet 170 having a sharps-penetrable envelope and containing wadding impregnated with a contaminant-neutralizing agent.

Although the invention has been described in detail with reference to certain embodiments, variations and modifications exist within the scope and spirit of the invention as described and defined in the following claims.

What is claimed is:

1. A block of material for penetration by, and for frictionally holding, contaminated sharps for disposal, a container for housing the block, the container having a bottom and a sidewall extending from the bottom, a lid for the container, the container including first engagement means and the lid including second engagement means for engaging the first engagement means to reduce the likelihood of disengagement of the lid from the container once the two are engaged, the container sidewall having a first depth and the lid sidewall having a second depth greater than the first depth.

2. The apparatus of claim 1 and further comprising a contaminant-neutralizing substance for impregnating the block.

3. The apparatus of claim 1 and further comprising an impregnable material located in the container and a contaminant-neutralizing substance for impregnating the impregnable material.

4. The apparatus of claim 3 wherein the block forms a first layer in the container, the impregnable material forms a second layer, and the second layer is positioned in the container between the first layer and the bottom.

5. The apparatus of claim 3 wherein the block forms a first layer in the container, the impregnable material forms a second layer, and the first layer is positioned in the container between the second layer and the bottom.

6. The apparatus of claim 3 wherein the impregnable material is impregnated with the contaminant-neutralizing substance and is contained within a sharps-penetrable envelope.

7. A block of material for penetration by, and for frictionally holding, contaminated sharps for disposal, a container for housing the block, the container having a bottom and a sidewall extending from the bottom, and means for mounting the container to a supporting surface, the mounting means comprising first means provided on the outside of one of the bottom and the sidewall of the container and complimentarily configured second means for mounting to a supporting surface, the first and second means configured for engagement to mount the container to the second means and for disengagement to facilitate removal of the container from the supporting surface, the second means comprising a base defining a central upwardly opening recess, a downwardly facing surface, a flexible strap extending from the base, and means on the base for engagement by the strap.

* * * * *